United States Patent [19]

Fráter et al.

[11] Patent Number: 4,947,002
[45] Date of Patent: Aug. 7, 1990

[54] TRICYCLIC KETONES AND FRAGRANCE COMPOSITIONS CONTAINING SAME

[75] Inventors: Georg Fráter, Uster; Urs Müller, Gossau, both of Switzerland

[73] Assignee: Givaudan Corporation, Clifton, N.J.

[21] Appl. No.: 266,036

[22] Filed: Nov. 2, 1988

[30] Foreign Application Priority Data

Nov. 12, 1987 [CH] Switzerland ................ 4425/87

[51] Int. Cl.⁵ ............................ C07C 49/317
[52] U.S. Cl. ............................ 568/373; 512/15
[58] Field of Search ........................ 568/373

[56] References Cited

U.S. PATENT DOCUMENTS

| 4,250,338 | 2/1981 | Sprecker et al. | 568/343 |
| 4,285,349 | 8/1981 | Sprecker et al. | 131/276 |
| 4,301,302 | 11/1981 | Sprecker et al. | 568/373 |
| 4,328,109 | 5/1982 | Sprecker et al. | 252/8.6 |
| 4,357,360 | 11/1982 | Light et al. | 426/538 |
| 4,368,128 | 1/1983 | Light et al. | 568/373 |
| 4,373,108 | 2/1983 | Light et al. | 568/373 |
| 4,411,830 | 10/1983 | Light et al. | 512/15 |

FOREIGN PATENT DOCUMENTS 0029259  5/1981  European Pat. Off. ............ 568/373

OTHER PUBLICATIONS

Barry Trost and Yoshiro Masuyama, Tet. Letters 25, (1984) 173-176.

Primary Examiner—James H. Reamer
Attorney, Agent, or Firm—Robert F. Tavares; Linda A. Vag

[57] ABSTRACT

Novel compounds of the formula

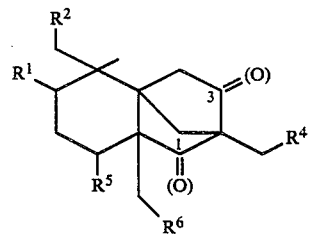

wherein:

the symbols $R^1$, $R^2$, $R^4$, $R^5$ and $R^6$ represent hydrogen or methyl, with the proviso that only one of $R^1$, $R^2$ and $R^4$ represents methyl, and, when either or both $R^5$ and $R^6$ represent methyl, then $R^1$, $R^2$ and $R^4$ represent hydrogen; and, either the symbol (=O) on the carbon designated by the number 1 or the symbol (=O) on the carbon designated by the number 3, represents a keto group, such that when the group is present on carbon 1, then carbon 3 may contain a methyl group.

and their use as odorants are described.

5 Claims, No Drawings

TRICYCLIC KETONES AND FRAGRANCE COMPOSITIONS CONTAINING SAME

SUMMARY OF THE INVENTION

The invention concerns novel odorants having the formula

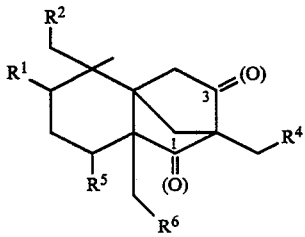

wherein:

The symbols $R^1$, $R^2$, $R^4$, $R^5$ and $R^6$ represent hydrogen or methyl, with the proviso that only one of $R^1$, $R^2$ and $R^4$ represents methyl, and, when either or both $R^5$ and $R^6$ represent methyl, then $R^1$, $R^2$ and $R^4$ represent hydrogen; and, either the symbol (=O) on the carbon designated by the number 1 or the symbol (=O) on the carbon designated by the number 3, represents a keto group, such that when the group is present on carbon 1, the carbon 3 may contain a methyl group.

Formula I represents both the hexahydro-2H-2,4a-methanonaphthalen-1(5H)-ones of formula Ia,

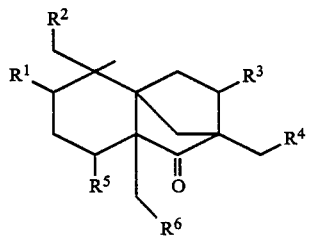

and the hexahydro-2H-2,4a-methanonaphthalene-3(4H)-ones of formula Ib

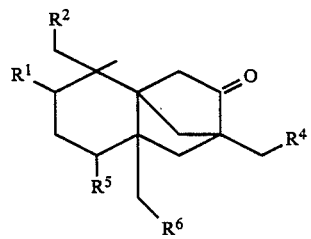

wherein $R^1$, $R^2$, $R^4$, $R^5$ and $R^6$ have the above significance and $R^3$ can be hydrogen or methyl.

The ketones of formula I possess very powerful, diffusive and very natural-warm, vetiver-like woody notes which make them particularly suitable for use as odorant substances. The invention, therefore, also concerns odorant substance compositions containing ketones of formula I.

The invention also concerns a process for the manufacture of the ketones of formula I which comprises oxidizing a compound of the formula

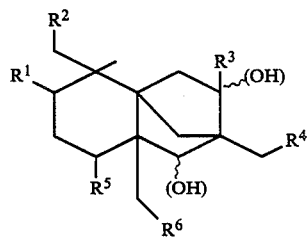

wherein $R^1$ to $R^6$ have the above significance and the brackets ( ) signify that only one hydroxy group is present in the molecule.

DESCRIPTION OF THE PREFERRED EMBODIMENTS

The oxidation of a formula II alcohol may be carried out by methods similar to those known in the art for the oxidation of a secondary alcohol to a ketone. Suitable oxidizing agents are, for example, chromic acid or Jones reagent, Javelle water (aqueous solution of sodium hypochlorite) and hydrogen peroxide ($H_2O_2$). It is preferred to use $H_2O_2$ as the oxidizing agent, preferably in the presence of ammonium molybdate as a catalyst. With the use of $H_2O_2$ it is also preferred to have present a phase transfer catalyst, such as the tetra-n-alkylammonium halides, and to conduct the oxidation at a temperature from about 20° to about 100° C.

The alcohols of formula II can be prepared according to the following reaction scheme wherein R designates a formyl or acetyl group. The alcohols of formula II and the esters of formula III are novel and also form part of the present invention. Because of their tricyclic structure, the compounds of formulas II and III may exist as a mixture of exo and endo isomers. The present invention is intended to embrace both of these isomeric forms.

Reaction Scheme

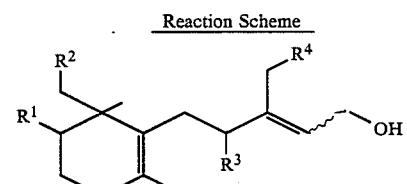

HCOOH or HCOOH/strong protonic acid
e.g. $HClO_4$, $H_2SO_4$, etc. or
$CH_3COOH$/strong protonic acid

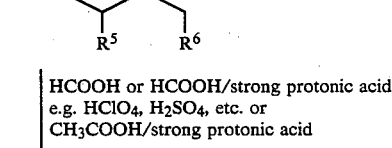

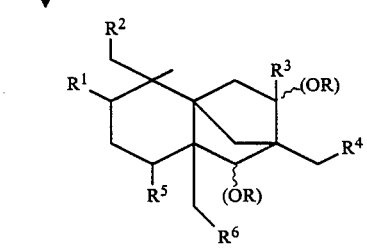

Hydrolysis (base/alkanol)

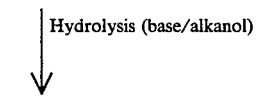

-continued
Reaction Scheme

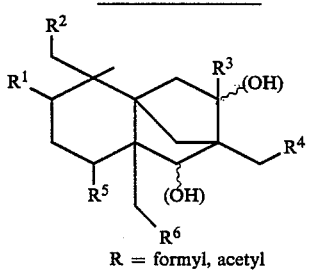

II

R = formyl, acetyl

The ratio HCOOH/strong protonic acid or CH₃COOH/strong protonic acid determines to large extent the ratio Ib:Ib which will be obtained. In general, the greater the amount of protonic acid used, the larger the amount of ketone IB that will be formed.

The separation of the mixture of ketones Ia and Ib obtained, can be effected by the usual methods for separation of a mixture of isomers such as by chromatography and/or recrystallization. It is not economical to do so however, and, for purposes of practice of the present invention, it is not necessary to do so, since the mixture of ketones. Ia and Ib may be used as such in odorant compositions.

It has been found that a ketone of formula V may also be formed in the reaction of alcohol IV and may, therefore, also be present in the product mixture in addition to the ketones of formula I. The presence of ketone V is somewhat dependent on the acids which are used.

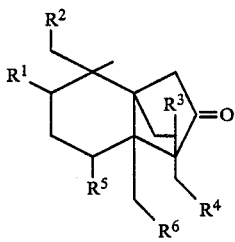

V

The symbols $R^1$ to $R^6$ have the previous significance.

Ketone V, which is likewise olfactorily active, can accordingly be used together with the mixture of ketones I usually obtained in accordance with the invention. The compounds of formula I are distinguished by very powerful, diffusive and very natural-warm, woody notes in the direction of vetiver. They exhibit a remarkable stability towards oxidizing agents and resistance towards weak acids and bases.

On the basis of their natural olfactory notes the compounds of formula I are especially suitable for modifying known compositions. In particular, their extraordinary olfactory strengths should be emphasized. The olfactory threshold value has been determined to be about 0.15 ng/l and the olfactory value has been determined to be 60,000–300,000. (For the definition of olfactory value and olfactory threshold value see for example, Ulrich A. Huber, Seifen - Oele - Fette - Wachse (i.e. Soaps - Oils - Fats - Waxes) 110, No. 15 (1984) 448–451.)

The compounds I combine with numerous known odorant ingredients of natural or synthetic origin, whereby the range of the natural odorants can embrace not only readily-volatile but also moderately-volatile and difficulty-volatile components and that of the synthetics can embrace representatives from practically all clases of substances, as is evident from the following compilation:

Natural products such as tree moss absolute, basil oils, citrus oils (such as bergamot oil, mandarine oil, etc.), mastix absolute, myrtle oil, palmarosa oil, patchouli oil, petitgrain oil Paraguay, wormwood oil, alcohols such as farnesol, geraniol, linalool, nerol, phenylethyl alcohol, rhodinol, cinnamic alcohol, Sandalore ® (Givaudan) (3-methyl-5-(2,2,3-trimethylcyclopent-3-en-1-yl)pentan-2-ol), aldehydes such as citral, α-hexylcinnamaldehyde, hydroxycitronellal, Lilial ® (Givaudan) (p-tert.-butyl-α-methyl-dihydrocinnamaldehyde), methylnonylacetaldehyde, ketones such as allylionone, α-ionone, β-ionone, isoraldeine (isomethyl-α-ionone), methylionone, esters such as allyl phenoxyacetate, benzyl salicylate, cinnamyl propionate, citronellyl acetate, citronellyl ethoxolate (citronellyl.O—CO—CO.OC₂H₅), decyl acetate, dimethylbenzylcarbinyl acetate, dimethylbenzylcarbinyl butyrate, ethyl acetoacetate, ethyl acetylacetate, hexenyl isobutyrate, linalyl acetate, methyl dihydrojasmonate, styrallyl acetate, vetiveryl acetate, Givescone ® (Givaudan), (2-ethyl-6,6-dimethyl (and 2,3,6,6-tetramethyl)-2-cyclohexene-1-carboxylic acid ethyl ester), lactones such as γ-undecalactone, various components frequently used in perfumery such as musk ketone, indole, p-menthane-8-thiol-3-one, methyleugenol.

Further, the manner in which the compounds round-off and harmonize the olfactory notes of known compositions, but without dominating in an unpleasant manner, is remarkable.

The compounds of formula I (or mixtures thereof) can be used in compositions in wide limits which can range, for example, from 0.1 (detergents)–20% (alcoholic solutions), without these values being, however, limiting values, as the experienced perfumer can achieve effects with even lower concentrations or can synthesize novel complexes with even higher amounts. The preferred concentrations range between about 1% and about 10%. The compositions manufactured with I can be used for all kinds of perfumed consumer goods (eau de cologne, eau de toilette, extracts, lotions, creams, shampoos, soaps, salves, powders, toothpastes, mouth washes, deodorants, detergents, tobacco etc.).

The compounds I can accordingly be used in the manufacture of compositions and - as the above compilation shows - using a wide range of known odorants or odorant mixtures. In the manufacture of such compositions the known odorants referred to above can be used according to methods known to the perfumer such as e.g. from W. A. Poucher, Perfumes, Cosmetics and Soaps 2, 7th Edition, Chapman and Hall, London 1974.

The compound I wherein $R^1=R^2=R^3=R^4=R^5=R^6=H$ is described as having woody, vetiver, peppery, rose and slightly fruity notes, and is preferred in the practice of the present invention.

The olfactory notes of the corresponding compounds are: IA: woody, agreste (i.e. rural, rustic: the smell of meadows, woods and fields, more particularly the fresh, pleasant and invigorating perfume one breathes in on strolling through meadows, woods and fields in the early morning of a spring day) with a fruity aspect;

Ib: woody, camphorous, pine, cedarous, with tobacco and fatty aspects;

V: woody, camphorous, earthy, borneol.

Further interesting compounds are:

(a) the corresponding compounds I with $R^1=CH_3$ and $R^2=R^3=R^4=R^5=R^6=H$ accessible from dihydro-β-irone, (b) the corresponding compounds I with $R^4=CH_3$ and $R^1=R^2=R^3=R^5=R^6=H$ accessible from dihydro-β-raldeine.

ILLUSTRATION OF THE PREFERRED EMBODIMENTS

A number of examples are provided herein to illustrate the preferred embodiments of this invention. The examples are included for the sole purpose of illustration and should not be construed as limiting. They are intended to embrace any equivalents or obvious extensions which are known or should be known to a person skilled in the art.

EXAMPLE 1

(a) Formic acid (98%), 2 l, is placed in a 4.5 l sulphonation flask, which is fitted with a reflux condenser, thermometer, dropping funnel, gas inlet tube and mechanical stirrer, and now treated dropwise at room temperature within 3 minutes with 444 g of the alcohol IV ($R^1=R^2=R^3=R^4=R^5=R^6=H$) (2 mol), whereby the temperature rises about 2° C. and a grey-brown solution results. The mixture is stirred at 40°–45° C. for a further 45 minutes. The educt disappears completely and the appearance of the formate III is established by gas-chromatographical analysis. This mixture is treated with water/ice, extracted with hexane, washed neutral, dried and evaporated; 542 g of a crude product are obtained. This crude product is fractionally distilled over a 5 cm Widmer column and fraction 2 of boiling point 90°–120° C./0.07 mmHg, which fraction weighs 252 g, is processed further.

(b) Formate III from step (a) (1 mol, 250 g) is added dropwise at 30° C. to 100 g of 85% KOH in 400 ml of methanol and 100 ml of water, whereby the temperature of the mixture rises to 63° C.; the mixture boils slightly. It is stirred at 65° C. water bath temperature for 30 minutes, cooled and poured into 2 l of ice-water; it is extracted three times with hexane and 20% t-butyl methyl ether, dried and evaporated, whereby 260 g of a crude product are obtained. This crude product is distilled in a high vacuum over a 10 cm Widmer column and the fraction of boiling point 93°–115° C./0.06 mmHg, which fraction weighs 23.5 g, is processed further. It is a thick viscous oil which hardens to a wax upon standing.

(c) The alcohol II of step (b) (150 g, 0.68 mol) is oxidized with 30% $H_2O_2$ in accordance with B. M. Troct et al., Tetr. Letters 25 (2), 173–176 (1984) in a 1 l three-necked flask, which is fitted with a thermometer, dropping funnel, condenser and stirrer. There is obtained 159 g of a blue-grey oil. This oil is now subjected to a high vacuum distillation; the fraction of boiling point 85°–87° C./0.09 mmHg is a product of olfactorily good quality. The ratio of ketone Ia to ketone Ib amounts to 7:2; this ketone mixture contains in addition 10% of the ketone V with $R^1$ to $R^6$=hydrogen. The separation into the components is effected by chromatography on silica gel using hexane/ether.

Physical data

Ketone Ia: $^{13}$C-NMR (CDCl$_3$): 222.9 (s,C-1), 53.9 (s,C-4a), 53.3 (s,C-2), 49.7 (s,C-8a), 42.4 (t,C-9), 38.99 (t,C-6), 32.78 (s,C-5), 32.44 (t,C-3), 30.86 (t,C-8), 27.55 (q,CH$_3$-C-5), 25.46 (t,C-4), 24.56 (q,CH$_3$-C-5), 19.49 (q,CH$_3$-C-8a), 18.01 (t,C-7), 14.82 (q,CH$_3$-C-2).

Ketone Ib: $^{13}$C-NMR (CDCl$_3$): 216.53 (s,C-2), 60.54 (s,C-1), 52.30 (s,C-3a), 47.85 (s,C-7a), 45.15 (t,C-3), 36.01 (t,C-5), 33.60 (s,C-4), 29.90 (t,C-8), 28.73 (q,CH$_{3,eq}$-C-4), 28.69 (t,C-7), 27.28 (t,C-9), 23.42 (q,CH$_{3,ax}$-C-4), 18.73 (t,C-6), 15.33 (q,CH$_3$-C-7a), 9.26 (q,CH$_3$-C-1).

Ketone V: $^{13}$C-NMR (CDCl$_3$): 215.0 (s,C-3), 53.66 (s,C-2), 53.28 (s,C-4a), 52.20 (t,C-1), 44.09 (t,C-9), 42.21 (t,C-4), 40.89 (t,C-8), 39.84 (s,C-8a), 38.23 (t,C-6), 33.09 (s,C-5), 29.19 (q,CH$_{3eq}$-C-5), 25.23 (q,CH$_{3ax}$-C-5), 24.55 (q,CH$_3$-C-8a), 19.61 (t,C-7), 14.58 (q,CH$_3$-C-2).

(c$_2$) The alcohol mixture of step (b) (0.2 mol, 44 g) is dissolved in 200 ml of glacial acetic acid in a 750 ml sulphonation flask, which is fitted with a thermometer, dropping funnel and stirrer and which is placed in an ice bath, and treated dropwise at 15°–20° C. while cooling with 90 ml of Javelle water (13–14% active chlorine), whereby the yellow phase remains for 5 minutes after the dropwise addition has finished. The mixture is worked-up with water and ether/hexane=2:8, thereupon washed with water and then with NaHSO$_3$ solution and extracted with 1N potassium hydroxide solution, the product is dried and evaporated, whereby 50.2 g of a crude product are obtained. Distillation in a high vacuum yields, after a fore-run, the fraction of boiling point 86°–88° C./0.08 mmHg (36.4 g) which is again rectified. There are obtained 34.9 g of a colourless oil I of boiling point 80°–81° C./0.06 mmHg.

(c$_3$) The alcohol mixture of step (b) (51 g, 0.232 mol) is dissolved in 300 ml of acetone while cooling by means of an ice/sodium chloride bath in a 1 l two-necked flask, which is equipped with a thermometer, dropping funnel and magnetic stirrer and which is placed in an ice/NaCl both, and treated at 5°–10° C. with 85 ml of Jones reagent until a slight orange colour remains. The mixture is stirred at room temperature for 1 hour and poured into 1 l of ice/water. The aqueous layer is extracted three times with 150 ml of hexane, washed with K$_2$CO$_3$ solution, dried and evaporated, whereby 56 g of oily crude product I are obtained. This is distilled in a high vacuum. There are obtained 46 g of colourless oil I of boiling point 85°–90° C./0.1 mmHg.

EXAMPLE 2

In the following formulations "compound I" stands for a mixture of Ia:Ib:V=7:2:1.

|  | Parts by weight |
| --- | --- |
| Geranium oxide (rose oxide) | 1 |
| Dimetol ® (Givaudan) (2,6-dimethylheptan-2-ol) | 9 |
| Citronellol extra | 10 |
| Givescone ® (Givaudan) | 10 |
| Methyl anthranilate extra | 10 |
| Geranylacetate | 20 |
| Coumarin pure cryst. | 20 |
| Vanillin | 20 |
| (3-(4'-Methoxy-phenyl)-2-methyl-propanal | 20 |
| Sandalwood essence | 30 |
| Eugenol extra | 30 |
| Phenylethyl alcohol | 40 |
| Ylang—ylang oil | 40 |
| Natural, purified aurantiol | 40 |
| Novalid ® (Givaudan) (1,4,6,8,8-Hexamethyl-as-hydrindacen-3-one) | 50 |
| Heliotropin cryst. | 50 |
| Compound 1 | 50 |
| Musk ketone | 60 |
| Benzyl acetate extra | 80 |
| Linalool synthet. | 80 |

-continued

|  | Parts by weight |
|---|---|
| Hydroxycitronellal | 100 |
| Methyl dihydrojasmonate | 110 |
| 3(and 4)-4-Methyl-4-hydroxyamyl)-Δ³-cyclohexene-carboxaldehyde | 120 |
|  | 1000 |

The compounds I confer volume, strength and body to the above composition. The spicy eugenol note is intensified.

|  | Parts by weight |
|---|---|
| Acetanisol | 10 |
| Eugenol extra | 10 |
| Cedar leaf oil | 10 |
| Anethol from star anis oil | 10 |
| Estragol | 10 |
| Phenylethyl alcohol | 20 |
| Citronellol extra | 30 |
| Lilial ® P (Givaudan) | 40 |
| Sandalore ® (Givaudan) | 40 |
| Linalool synthet. | 40 |
| Musk moskene | 40 |
| Orange oil Florida | 60 |
| Benzyl acetate extra | 60 |
| Linalyl acetate synthet. | 60 |
| Benzyl salicylate | 100 |
| Novalid ™ (Givaudan) | 120 |
| α-Hexylcinnamaldehyde | 140 |
| Compound 1 | 200 |
|  | 1000 |

The compound I produces strength, fullness and volume in this base.

|  | Parts by weight |
|---|---|
| 2,6-Nonadienal (1% diprocol) | 2 |
| Galbanum oil natural | 3 |
| Eugenol extra | 5 |
| 4-Isopropyl-cyclohexanol | 10 |
| cis-3-Hexenol (10% diprocol) | 10 |
| Phenylacetaldehyde (10% diprocol) | 10 |
| Compound 1 | 20 |
| Musk moskene | 20 |
| Cedarwood oil Virginia | 20 |
| Methyl octyne carbonate (10% diprocol) | 20 |
| Givescone ® (Givaudan) | 20 |
| Geranium oil Bourbon | 50 |
| Lilial ® P (Givaudan) | 50 |
| Benzyl acetate extra | 50 |
| α-Irisone | 50 |
| Methyl dihydrojasmonate | 50 |
| p-tert.Butylcyclohexyl acetate | 80 |
| Geraniol extra | 80 |
| Citronellol extra | 150 |
| Phenylethyl alcohol | 300 |
|  | 1000 |

The compound I intensifies the lily of the valley note in a distinct manner. The compound I produces quite generally volume, diffusion, naturalness, harmony, strength.

We claim:
1. A compound of the formula

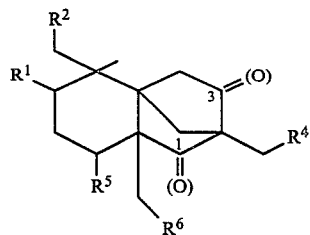

wherein:
the symbols $R^1$, $R^2$, $R^4$, $R^5$ and $R^6$ represent hydrogen or methyl, with the proviso that only one of $R^1$, $R^2$ and $R^4$ represents methyl, and, when either or both $R^5$ and $R^6$ represent methyl, then $R^1$, $R^2$ and $R^4$ represent hydrogen; and,
either the symbol (=O) on the carbon designated by the number 1 or the symbol (=O) on the carbon designated by the number 3, represents a keto group, such that when the group is present on carbon 1, tthen carbon 3 may contain a methyl group.

2. A compound according to claim 1 having the formula

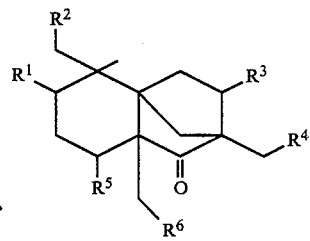

wherein:
$R^3$ also represents hydrogen or methyl, with the proviso that only one of $R^1$ to $R^4$ represents methyl, and, when either or both $R^5$ and $R^6$ represent methyl, then $R^3$ represents hydrogen.

3. The compound according to claim 2 which is hexahydro-2,5,5,8a-tetramethyl-2H-2,4a-methanonaphthalen-1(5H)-one.

4. A compound according to claim 1 having the formula

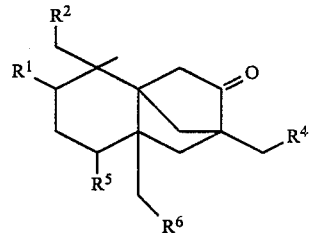

5. The compound according to claim 4 which is hexahydro-2,5,5,8 a-tetramethyl-2H-2,4a-methanonaphthalen-3(4H)-one.

* * * * *